United States Patent [19]

Lipshitz

[11] Patent Number: 4,783,335
[45] Date of Patent: Nov. 8, 1988

[54] CONTROLLED TOPICAL APPLICATION OF BIOACTIVE REAGENT

[75] Inventor: Harold M. Lipshitz, Carlisle, Mass.

[73] Assignee: The Kendall Company, Boston, Mass.

[21] Appl. No.: 904,764

[22] Filed: Sep. 5, 1986

Related U.S. Application Data

[63] Continuation of Ser. No. 799,037, Nov. 18, 1985, abandoned.

[51] Int. Cl.⁴ ............... A01N 25/24; A61K 31/78
[52] U.S. Cl. ................................. 424/407; 424/81; 514/965
[58] Field of Search ............ 424/81, 12, 407, 487; 514/965

[56] References Cited

U.S. PATENT DOCUMENTS

| | | | |
|---|---|---|---|
| 3,235,366 | 2/1966 | Seymour et al. | 424/81 |
| 3,590,118 | 6/1971 | Conrady et al. | 424/81 |
| 4,007,258 | 2/1977 | Cohen et al. | 424/81 |
| 4,177,056 | 12/1979 | Mueller et al. | 424/81 |
| 4,225,693 | 9/1980 | McCormick | 424/81 |
| 4,282,209 | 8/1981 | Tocker | 424/81 |
| 4,304,591 | 12/1981 | Mueller et al. | 424/81 |
| 4,411,754 | 10/1983 | Kaetsu et al. | 424/81 |
| 4,470,966 | 9/1984 | Costanza et al. | 424/81 |
| 4,543,251 | 9/1985 | Kamishita | 424/81 |
| 4,548,990 | 10/1985 | Mueller et al. | 424/81 |

*Primary Examiner*—Douglas W. Robinson
*Attorney, Agent, or Firm*—Alvin Isaacs

[57] ABSTRACT

Novel compositions for topical application of a water-insoluble bioactive reagent, e.g. a pesticide, comprising an aqueous emulsion of a polymer swellable by the sebum and other "skin oils" and which will agglomerate or coagulate near the skin, the polymer having the bioactive agent encapsulated or dispersed therein; and novel methods employing the same for controlled release of the bioactive reagent over an extended period of time.

27 Claims, No Drawings

CONTROLLED TOPICAL APPLICATION OF BIOACTIVE REAGENT

This application is a continuation of Ser. No. 799,037 filed Nov. 18, 1985, now abandoned.

It is frequently necessary to apply a bioactive reagent, e.g. an insecticide or fungicide, to the skin of animals. For example, it may be necessary to protect farm animals such as cattle, horses, sheep, etc. from parasitic insects over extended periods of time.

The problems that parasitic insects can cause to farm animals are most pronounced in the Southern hemisphere, e.g. Africa and certain countries in South America. Apart from the possible dangers of disease transmission by ticks, lice and the like, these insects present a substantial danger to the health of the animals that often results in weight loss. In beef-producing regions where parasitic invasion of the animal skin is most prevalent, the magnitude of the problem can be best understood.

To obviate this problem it has heretofore been known to treat the animals with a pyrethroid insecticide. This is typically done by spraying or dousing the animals with an agueous suspension of the active reagent.

While this procedure can be effective against the insects, it nevertheless suffers from certain deficiencies inherent to the mode of topical application. Skin sores frequently occur, causing discomfort to the animals, attracting flies and even producing infections. Moreover, the treatment is of a short duration, e.g. on the order of one week or less, and this in turn requires frequent rounding up and retreatments of the animals, a laborious and expensive procedure.

It would therefore be most desirable to find some solution to the aforementioned problems wherein the pyrethroid or other bioactive reagent can be released in a controlled manner over an extended period of time, thereby both minimizing injury due to initial contact with high concentrations and also materially reducing the frequency of topical applications. As will be appreciated, the ability to reduce the frequency of application is most important from an economic point of view.

The concept of controlled release of bioactive reagents for topical and transdermal application is per se not new.

For example, procedures are known for the controlled release of a drug or medicament from bandages, dressings and adhesive compositions applied to the skin. As examples of such procedures, mention may be made of those described and claimed in U.S. Pat. Nos. 3,577,516 of Gould et al; 3,579,628 of Gander et al; 3,734,097 of Zaffaroni; and 4,310,509 of Berglund. The disadvantages of these products as applied to the treatment of livestock are readily apparent. Consequently, these systems provide no viable solution to the problem to which this invention is primarily directed.

U.S. Pat. No. 3,590,118 of Conrady et al relates to long-lasting insect repellent solutions which are applied as ammoniated water solutions or organic solvent solutions and which when dried form a thin water-insoluble film that slowly releases the insect repellent. The solutions are water-insoluble, alkaline-water soluble compositions of the insect repellent and specified thermoplastic resins.

Other systems for controlled release of a drug or medicament utilize a composition including a polymer which swells in the presence of moisture, e.g. moisture emitted from a body tissue such as the mucosa. For example, U.S. Pat. No. 4,292,299 issued to Suzuki et al discloses a slow-releasing medical preparation to be administered by adhering to the wet mucous surface, comprising an adhesive layer composed of a polymer which adheres to the wet mucous surface and swells upon moistening; and a nonadhesive, either water soluble or disintegratable layer which has no adhesiveness to the wet mucous surface, at least one of these layers containing a medicament. U.S. Pat. No. 4,059,686 to Tanaka relates to a pharmaceutical preparation for oral cavity administration with superior adhesion to local sites, comprising a pharmacologically active agent, a pharmaceutical carrier and sodium polyacrylate. This preparation adheres firmly to a local site and dissolves gradually over a long period of time to release the medicinal agent for absorption through the oral mucous membrane. U.S. Pat. No. 4,226,848 and a division thereof, 4,250,163 discloses a pharmaceutical preparation adhering to the mucosa of the oral or nasal cavity and which comprises a medicament dispersed in a specified water-swellable and mucosa-adhesive polymeric matrix.

U.S. Pat. No. 4,374,126 issued to Cardarelli et al teaches a topical antiseptic preparation for preventing infection of human and other animal tissue and which is resistant to physical removal, but is easily removed by soap and water. The composition contains one or more antimicrobial agents as well as adhesives to enhance topical application. Upon evaporation of the carrier solvent, an effective long lasting topical film containing antimicrobial agents is provided.

U.S. Pat.No. 4,409,206 to Stricker teaches a pharmaceutical preparation for transdermal application, comprising a film of a skin-compatible polyacrylate that swells in water and a pharmaceutically active substance in amorphous form.

Finally, U.S. Pat.No. 4,490,322 issued to Zierenberg relates to a preformed or packaged pharmaceutical film for long term transdermal administration of systemic pharmaceuticals comprising a homogeneous solution of the pharmaceutical and a specified freeze-dried latex.

While not intended to be a complete or exhaustive study of the relevant prior art, the foregoing citations are nevertheless considered to be both illustrative and representative of the state of the art known to applicant for extended or long term administration of a bioactive agent.

None of these prior art teachings discloses or suggests a solution to the problem which is the task of the present invention, namely the topical application of a water-insoluble bioactive agent, particularly a pesticide, to cattle and other livestock to provide an effective amount of the reagent over an extended period of time, thereby reducing the frequency of required applications and also the adverse effects, e.g. skin sores, etc., which can occur when the initial topically applied preparation releases for dermal contact injurious concentrations of the effective ingredient.

The prior systems utilizing bandages, tapes, films and the like are obviously not feasible. Clearly, they are not efficacious for topical application over the animal skin to protect the animal from parasitic insects and the like.

Likewise, systems utilizing water-soluble or water-swellable compositions have not been found to be useful, due to the insolubility of the contemplated pesticide or other bioactive reagent.

The present invention provides a simple and highly efficient solution to this problem.

SUMMARY OF THE INVENTION

In accordance with the present invention, compositions for topical application to animals are provided comprising an agueous emulsion of a polymer having a bioactive agent retained or encapsulated therein, the polymer particles being characterized by agglomeration and/or coalescence on solvent evaporation and by being swellable by skin oils. As used herein and in the appended claims, the term "skin oils" refers to sebum and/or skin lipids of host origin.

To be effective for its intended purpose, the composition must be applied and then agglomerate or coalesce on or near the animal skin in maximal physical proximity with the skin oils, rather than on the surface of the animal hairs which contain relatively small amounts of these skin oils. Thus, while the aforementioned polymer and bioactive reagent constitute the essential ingredients for topical application in general, for effective application to cattle and the like, means must also be included for permitting the applied agueous emulsion rapidly to penetrate through the animal hairs and to the skin before significant quantities agglomerate or coalesce on the hairs rather then on the skin. In other words, to be effective, the applied solution must penetrate in closest proximity to the skin surface.

It has been found that incorporating a reagent facilitating rapid transport by capillary action through the hair and to the skin where it then agglomerates and/or coalesces is an effective means. Useful reagents for this purpose are anionic and non-ionic surfactants, the latter being preferred.

DETAILED DESCRIPTION OF THE INVENTION

As was mentioned previously, the present invention is directed to novel compositions and procedures for topical application of an essentially water-insoluble bioactive agent to the skin of animals, particularly farm animals and livestock such as cattle, sheep, horses and the like. Since the need of this topical application is particularly acute in the Southern hemisphere, the invention can best be understood and the importance thereof best appreciated by reference thereto for purposes of illustration.

The raising and production of beef is a very large industry in certain countries in the Southern hemisphere, e.g. South Africa, and Argentina and other countries in South America. These countries inherently have large populations of parasitic insects, e.g. ticks, which present real problems for the herds of livestock. Apart from the inherent dangers of being carriers of disease which can spread through the herds, prolonged and excessive invasion of the animal skin tends to produce weight loss, thereby diminishing the value of the animal for slaughter. Consequently, it is customary to round up the animals on a frequent basis, e.g. weekly, and subject them to spraying, dipping or pouring down their backs an agueous solution or suspension of an effective pesticide. Many pesticides, e.g. the known pyrethroid pesticides are highly effective for this purpose. However, the aforementioned customary modes of topical application are relatively short lived, e.g. on the order of a week or less, thereby requiring frequent, expensive and time-and-labor-consuming efforts in rounding up and treating the animals.

Moreover, to insure effective administration of the active reagent, the topical solutions or suspensions typically contain concentrations of pesticide or other active reagent in excess of the required effective amount and these higher concentrations frequently produce skin irritations or sores which, in turn, cause discomfort, attract flies, and produce infections.

It is therefore most desirable to devise a way for topical administration of these per se known active agents so that the treatment lasts over an extended period of time to reduce the frequency of required treatments. Most preferably, the release rate of the active agent should be controlled so that excessive amounts do not initially contact the skin and the amount so released remains effective over this extended period of time. In other words, if release rates were to be plotted on a graph with the time in days or weeks measured on the abscissa or X axis and the amount released on the ordinate or Y axis, optimally the curve should be a substantially horizontal straight line for a period of time and then gradually curve down until it shows a level below effective concentrations, thereby indicating the duration of effective treatment.

As previously discussed, the known procedures for administration, e.g. those mentioned in the illustrative citations, are not applicable for solving the task of this invention.

It is to this problem to which the present invention is primarily directed.

According to this invention, the problem is solved simply and efficiently by providing an agueous emulsion, preferably of low viscosity for ease of topical application, of the pesticide or other active agent dispersed in a polymer characterized as being swellable by the skin oils and when so swelled to release the dispersed active agent within the skin oils where it is then transported, by diffusion, across the body surface. The polymer is further characterized as being able to agglomerate and, in some cases, to form a film on the skin surface, thus reducing the release rates for the contained reagent and thereby prolonging the effective duration of the topical application.

As will be appreciated, as used herein the term "effective" refers to the capability of performing or accomplishing the desired effect. Thus, "effective amount" denotes the amount needed to obtain a desired result; and "effective duration" refers to the period of time for obtaining this result.

While perhaps not capable of a precise chemical definition or analysis, the skin oils are understood in the art to consist generally of sebum, a secretion of the sebaceous glands in the form of a thick semi-fluid substance composed of fat and epithelial debris from the cells of the malpighian layer, as well as other lipid materials of host origin found on the skin. More simply, it can be described as an oily or greasy lubricating substance secreted by the animal. In determining the useful polymers for the practice of this invention, it is not necessary, however, to maintain supplies of these skin oils in the laboratory for experimental purposes. Sesame oil has been found to be a model substance for this purpose. It can accordingly be said that generally, polymers swellable in sesame oil would be swellable in the skin oils and their use may therefore be contemplated.

As was mentioned, in addition to being swellable by skin oils to release the active agents, the polymer particles should coalesce or agglomerate upon deposit on the skin. This is necessary since the release rates of agents from polymeric matrices depend, among other factors, upon the size and geometry of the polymeric particles. If the polymer does not agglomerate to form a sufficiently large particle or film, the release rate of the bioactive reagent would be so rapid as to defeat the task of continued release of effective amounts over an extended period of time.

As was also mentioned, the "film-forming" skin oil-swellable polymeric particles having the active agent dispersed therein should be deposited predominantly on or near on the skin surface for proximity to the skin oil source and not on the body hairs of the animal. The ability to so penetrate the animal hairs is in part a function of particle size and for optimum efficiency particles of the order of 50 microns or less should be employed.

The ability of the polymeric particles to pass through the hair to the skin is also in part dependent upon their ability to do so before they coalesce to form a film or agglomerate on the hairs. In other words, even if particles no greater than 50 microns are employed, a great number of them would tend to become entrapped on the hair upon coalescence unless they are drawn or penetrate to the skin fairly rapidly before significant coalescence can occur. Otherwise, the liquid containing the dispersed reagent will tend to flow off the body of the animal. Accordingly, with animals where the body hairs present this inherent problem, e.g. cattle, the agueous emulsion should further contain a reagent facilitating or assisting the capillary flow of the polymeric particles with dispersed active agent. Useful reagents for this purpose include anionic and non-ionic surfactants, the latter being preferred.

It should be understood, however, that the need for a surfactant does not necessarily exist in the topical treatment of all animals to which the present invention is directed. Where found advisable or necessary to employ a surfactant, it will be appreciated that the amounts so employed may vary for the treatment of different animals. In any event, the novel compositions of this invention can be initially manufactured and sold surfactant-free, in which case the proper amounts of surfactant can be admixed, if needed, at some time prior to use.

To recapitulate, the polymeric bioactive agent containing particles in the agueous emulsions of this invention should optimally have a particle size no greater than 50 microns in diameter for penetration through the animal hair to the skin. However, as will be appreciated by those skilled in the art, the release rate of the bioactive agent entrained or dispersed therein is inversely proportional to the size of the polymeric particle. Consequently, if the particles were simply present on the animal skin as discrete deposits, swelling by the skin oils would result in a very rapid release of the bioactive agent, thereby defeating the primary object of this invention. Consequently, it is necessary that the particles agglomerate on the skin surface, to prolong and thereby control the release over an extended period of time, say, for example, a month or more.

The rate of release which should be employed in the practice of this invention is not capable of precise quantitative measurements, but will in general be dependent upon the levels desired to be maintained for treatment and this in turn may vary from reagent to reagent according to the efficiency or effectiveness of the reagent for that purpose. For example, the bioactive agent may be a fungicide, a bactericide or an insecticide. For each of the above groups, different levels of dosage or periods of duration may be contemplated and, moreover, the concentrations desired within a given class of reagents may well vary according to the particular reagent selected. In other words, a given pyrethroid insecticide may require one level or amount of application to be effective; and another one may require greater or lesser amounts.

In any event, the selection of desired levels of release will be readily apparent to those skilled in the art. Once the desired level is ascertained for the particular reagent to be employed, the release rate to achieve this level may be obtained, other factors remaining the same, by judicially adjusting the cross-link density within the polymeric mixture. In general, the release rate is inversely proportional to the degree of cross-linking so that the greater the cross-link density, the slower the release rate. It will be appreciated, however, that if the cross-link density is too great, diffusion within the polymeric "barrier" will be so slow as to render the contained reagent effectively unreleasable. As will also be appreciated, the overall average release rate may be adjusted by admixing particles with varying degrees of cross-linking and/or particles with no cross-linking with particles which are cross-linked in the same or in different degrees.

In any event, it will again be understood that, as a generalization, the degrees of cross-linking and/or the proportions of differently cross-linked particles which may be admixed cannot be reduced to precise mathematical terms and, indeed, any attempt to do so could be inaccurate or misleading. Numerical values applicable to one system may be totally inappropriate to another.

Their selection involves only routine experimentation within the expected judgement of the skilled worker and hence can be readily derived without the exercise of inventive faculties in the light of the foregoing description and the illustrative examples which will follow.

The selection of useful skin oil-swellable and agglomeratable polymers will also be apparent to the skilled worker. The preferred are copolymers of acrylic esters and acrylic acid, e.g. a terpolymer of 2-ethylhexylacrylate, ethyl acrylate and acrylic acid. The proportions of the monomers may of course vary within the above parameters, namely sebum-swellable and agglomeratable. By way of illustration, a terpolymer of the above three monomers in a ratio by weight of 30:8:1 have been found to be particularly useful. Other momomers which may be employed, the selection of which per se comprises no part of this invention, will be readily apparent to those skilled in the art. By way of further, illustration, such useful monomers include vinyl acetate, ethyl acrylate, methyl acrylate, etc.

As was mentioned earlier, the rate of swellability and hence the release rate may be controlled by judicious cross-linking. While in general, it can be said that the various cross-linking agents generally known in the polymer chemistry field may be employed for this purpose, difunctional monomers added during polymerization, such as ethylene glycol dimethacrylate, are particularly efficaceous. Other useful cross-linking agents include butylene glycol dimethacrylate, bis methylene acrylamide, etc. As stated, the degree of cross-linking may vary considerably in accordance with the ingredients employed and the release rates desired. By way of illustration, however, weight ratios of ethylene glycol dimethacrylate with respect to the total weights of the monomers of the aforementioned terpolymer of the order of 1:90 to 1:525, have been found useful. If found expedient or desirable to do so, the polymeric compositions employed in the practice of this invention may comprise a blend of varying proportions of polymer particles with different degrees of cross-linking in order to arrive at a blend having a particularly desired release rate.

Apart from the stated particle size, it is necessary, at least with certain animals, to include an anionic or nonionic surfactant in order to permit the polymeric dispersion to penetrate the body hairs to the animal skin before agglomeration occurs to form an agglomerate of the dispersion at or near the skin. It is not essential, however, that all of the dispersion penetrate the body hairs. Indeed, although experimentation has not been performed, it may in fact be advantageous that some quantity, e.g. an amount less than, say, 10 percent be present on the body hairs and thus slowly be released over a period of time, in order to extend the effective duration of a given treatment. The preferred are the known nonionic surfactants such as the monoglycerides of higher fatty acids, octoxynols such as Triton X-100 (trademark of Rohm & Haas), etc. In general, percentages of surfactant on the order of about 3%, by volume, of the emulsion are preferred.

The bioactive agents which may be employed in the practice of this invention will in general comprise the known reagents for topical application. However, as mentioned previously, the present invention is particularly directed to the treatment of cattle and other livestock to prevent the harmful effects of ticks and other blood-sucking parasites. Pyrethroid insecticides have been recognized as being especially useful pesticides for this purpose. A preferred pyrethroid insecticide is cypermethrin, commercially available from FMC Corporation.

The bioactive agent may be dispersed or incorporated in the polymeric component in a variety of ways. It may, for example, be encapsulated within a polymeric skin or wall. A particularly expedient way is to disperse the reagent in one of the liquid monomers and then add the remaining monomers and polymerize in per se known manner.

The following examples show by way of illustration and not by way of limitation useful compositions embodying the present invention.

EXAMPLE 1

Three separate solutions were provided: (1) a monomer premix solution; (2) a reductant solution; and (3) a reaction solution. The monomer premix solution was formed by dissolving 29.89 g (5.0 pph) of the ectoparasiticide, cypermethrin in a solution of 426.0 g (71.2 pph) of 2-ethyl hexyl acrylate, 113.6 g (19.0 pph) of ethyl acrylate, 14.2 g (2.37 pph) of acrylic acid, 47.3 g (2,38 pph) of the surfactant, Alipal EP-110, 255.6 g of a one percent aqueous solution of tertiary butyl hydroperoxide (initiator) and 35.5 g of deionized water. The reductant solution consisted of 170.4 g of a one percent aqueous solution of sodium formaldehyde sulfoxylate. The reaction solution consisted of 14 deps. of a one percent aqueous solution of ferric ammonium sulfate dissolved in 1562.0 g of deionized water. All three solutions were purged of dissolved oxygen by bubbling nitrogen through the solutions for at least thirty minutes. Approximately 10% percent of the monomer premix and reductant solutions were added to the reaction solution under a nitrogen atmosphere. The remaining 90% of the monomer premix and reductant solutions were added to the reaction mixture under a nitrogen atmosphere over a two hour period. The temperature was maintained throughout the reaction between 38° and 42° C. by the circulation of thermostated water round a jacket enclosing the reaction container. After the addition of the monomer premix, the temperature of the solution was maintained at 40° C. with agitation for one hour. The resulting yield provided about 2655 grams of an aqueous emulsion of the terpolymer of 2-ethyl hexyl acrylate (63.5 mole percent), ethyl acrylate (31.1 mole percent) and acrylic acid (5.4 mole percent) having the ectoparasiticide, cypermethrin, contained therein. Analysis: theoretical solids, 22.52%; measured solid, 22,5%; 1% of polyerm coagulated; conversion (by residual monomers), 99.86%.

EXAMPLE 2

Example 1 was repeated, except that the monomer premix consisted of: 29.96 g (4.99 pph) of cypermethrin, 426.0 g (71.0 pph) of 2-ethylhexylacrylate; 113.6 g (18.9 pph) ethyl acrylate, 14.2 g (2.37 pph) of acrylic acid, 1.065 g (0.18 pph) of ethylene glycol dimethacrylate, 49.7 (2.49 pph) of Alipal EP-110, 255.6 g of a one percent aqueous solution of tertiary butyl hydroperoxide, and 35.5 g of deionized water. The total batch was about 2658 of an aqueous emulsion of the terpolymer of 2-ethylhexylacrylate (63.4 mole %), ethyl acrylate (31.1 mole %) and acrylic acid (5.4 mole % cross-linked with ethylene glycol dimethacrylate (0.2 mole %), containing cypermethrin. Analysis: theoretical solids, 22.56%; measured solids, 22.3%; 1% of polymer coagulated; conversion (by residual monomers), 99.86%.

EXAMPLE 3

Example 2 was repeated, except that 29.89 g (4.97 pph) of cypermethrin, 3.00 g (0.50 pph) of ethylene glycol dimethacrylate, and 47.36 g (2.36 pph) of Alipal EP-110 were employed in the monomer premix in lieu of the amounts recited in Example 2. The total batch of about 2658 g provided an aqueous emulsion of the terpolymer of 2-ethylhexylacrylate (62.2 mole %), ethyl acrylate (30.4 mole %) and acrylic acid (7.1 mole %) cross-linked with ethylene glycol dimethacrylate (0.4 mole %) having the ectoparasiticide contained therein. Analysis: theoretical solids, 22.61%; measured solids, 20.4%; 1% of polymer coagulated; conversion (by residual monomers) 99.77%.

EXAMPLE 4

Example 1 was repeated using the following ingredients for the three solutions:

| Monomer Premix | Gram | Solids, Comp., PPH |
|---|---|---|
| Cypermethrin | 2.00 | 2.42 |
| 2-ethylhexylacrylate | 60.00 | 72.50 |
| Ethyl acrylate | 16.00 | 19.30 |
| Acrylic acid | 2.00 | 2.42 |
| Ethylene glycol dimethacrylate | 0.80 | 0.97 |
| Alipal EP-110 | 6.67 | 2.42 |
| Deionized water | 5.00 | |
| Reductant | | |
| 1% aqueous sodium formaldehyde sulfoxylate | | 24.0 |
| Reactor | | |
| deionized water | | 22.0 |
| 1% aqueous ferric ammonium sulfate | | 2 dps. |

The total batch of about 372 grams provided an aqueous emulsion of the terpolymer of 2-ethylhexylacrylate (63.2 mole %), ethyl acrylate (31.0 mole %) and acrylic acid (5.3 mole %) cross-linked with the dimethacrylate (0.5 mole %) having the ectoparasiticde, cypermethrin, contained therein. Analysis: theoretical solids, 22.20%; measured solids, 20.8%; 6.6% of polymer coagulated.

It will be noted in the foregoing examples that a anionic surfactant, Alipal EP-110, was employed in the preparation of the emulsion, e.g. for the polymerization step to prepare the emulsion. In the context of this invention, the resulting emulsion does not contain a surfactant, as referred to previously, in order to permit the polymeric dispersion to penetrate the body hairs to the animal skin before agglomeration occurs. In the treatment of animals requiring a surfactant for this purpose, the surfactant may be added to the emulsion at any time prior to use.

For purposes of illustration, in each of the emulsions prepared in Examples 1–4, 3% by emulsion volume, of the nonionic surfactant, Triton X-100 was added to provide an ectoparasiticide preparation suitable for the treatment of cattle.

In the foregoing examples, the bioactive reagent was dispersed in one of the liquid monomers prior to polymerization.

In the following example, it was incorporated within the particles of a previously formed polymer.

EXAMPLE 5

40.0 gms. of Elvax-250 (trademark of E.I. du Pont de Nemours for an ethylene-vinyl acetate copolymer understood to contain 20% by weight vinyl acetate) were dissolved in 300 ml. (258 gms.) of mixed (ortho-meta-, and para-) xylene at 60° C. The solution was cooled to 23° C. and 4.0 gms. of cypermethrin were then added. A 5% by weight aqueous solution of Alipal EP-110 surfactant was then dripped into the resulting xylene solution under high speed stirring, using a Gifford-Wood homogenizer to form a so-called water in oil emulsion. When around 36% by weight of the aqueous solution was added to the xylene, phase inversion occurred such that the polymeric (ethylene-vinyl acetate) particles, swollen with xylene and having the cypermethrin incorporated within them, were dispersed in the water.

3% by volume of Triton X-100 was then added, as previously described, to permit the polymeric particles rapidly to penetrate the animal hairs to the skin level.

In penetration, the particles agglomerated to form large film-like particles adjacent the skin.

The efficacy of the present invention in providing the controlled release of effective amounts of a water-insoluble bioactive reagent over an extended period of time was initially confirmed by in vitro tests.

In the following examples, a piece of hide (approx. 8x10 cm) obtained from a freshly killed steer and which contained its natureal hairs, was utilized in order to simulate in vivo experimentations as closely as was reasonably feasible. A portion of this hide was shaved in order to facilitate collection and measurement of the released reagent. As a substitute for the skin oils which would be normally present on a live steer, the hide was coated with a thin layer of sesame oil.

EXAMPLE 6

A quantity of the test preparation of Example 1 was applied to a hairy region so as to provide 14.57±0.1 mg. of applied cypermethrin. After 24 hours, a quantity of sesame oil from the shaved portion was extracted in order to ascertain the amount of cypermethrin which was present therein by lateral diffusion from the hairy region where the preparation was applied. Analysis found 0.7±0.5 mg. (4.5±2.9% of the applied quantity).

EXAMPLE 7

The above procedure was repeated, substituting the preparation of Example 2 to provide 15.87±0.07 mg. of applied reagent. Found: 0.45±0.05 mg. (2.8±0.3%).

EXAMPLE 8

The above procedure was repeated, substituting the perparation of Example 3 to provide 12.26±0.5 mg. of applied reagent. Found: 0.26 1 0.20 mg. (2.3±1.6%) of reagent.

The foregoing in vitro tests establish that effective amounts of the active reagent (in this case, cypermethrin) are present on the hide after twenty-four hours. Moreover, the amounts found are not excessive on a percentage basis, indicative of the presence in the hairy applied portion of yet-to-be released quantities.

The following example illustrates another form of in vitro test which may be employed in the determination of the efficacy of the invention.

EXAMPLE 9

The polymeric particles were dispersed in sesame oil under mild agitation at concentrations that ranged from 1 to 5% by weight with respect to the sesame oil. At periodic intervals, samples of the dispersions were withdrawn, centrifuged and the concentration of cypermethrin in the sesame oil determined. The cypermethrin concentrations were determined by dissolving the sesame oil containing some dissolved cypermethrin in hexane at concentrations of around 25 to 100 mgm of solution in 10 to 25 ml. of hexame (depending upon absorbances) and then measuring the absorbance of the solution at 278 mm. [This assumed the absorbance of the sesame oil to be negligible under these conditions. At this wavelength, the extinction coefficients of the respective compounds, cypermethrin and the constituents of sesame oil, differ by a factor of 1000.]

Alternatively, the absorbances at two wavelengths were determined (278 and 258 m$\mu$, thereby taking into account the absorbance of the sesame oil. Since the measurements were done in the range of absorbance where Beer's law held at the two wavelengths selected, the contribution to the total absorbance at each respective wavelength due to sesame oil could be determined by solving two linear equations simultaneously for the concentrations of the ectoparasiticde and the sesame oil.

In Examples 6–9, reference is made to in vitro experimentations.

Ih vivo tests further confirmed the efficacy of the present invention. A composition prepared according to Example 3 containing 3% by emulsion volume of the surfactant, Triton X-100 was applied, by dousing, to a plurality of cattle in South Africa. The ectoparasiticde treatment was found to be effective in protecting the animals for one month.

From the foregoing description and illustrative examples, it will thus be seen that the present invention provides an elegant and highly efficaceous means for the topical application to the skins of animals of a bioactive reagent which should be present in effective amounts for an extended period of time.

While reference has been made in the illustrative examples to the topical application of an ectoparasiticide, cypermethrin (cyclopropanecarboxylic acid, 3-(2,2-dichloroethenyl) -2,2-dimethyl-cyano (3-phenoxyphenyl) methyester, C.A. Reg. No. 52315-07-8), it should be readily appreciated that the invention is not so restricted. It is to be expressly understood that patentable novelty is not herein predicted upon the selection of any particular bioactive reagent and the use of the per se known substantially water-insoluble bioactive reagents, e.g. pesticides, (used in the generic sense to include pyrethroids, ectoparasiticides and the like), fungicides, bactericides, insect repellants, pharmaceuticals and other chemicals heretofore applied to animal skins for known purposes are also contemplated by the present invention. It will of course be inherent in the practice of this invention that th selected reagent should be non-reactive in the preparation of the emulsions to which this invention is directed, i.e. should not react with the monomers or other materials employed in the preparation of these compositions so as to adversely effect its ability to function as intended.

Since certain changes may be made in the compositions and procedures recited in the foregoing description without coating from the scope of the invention, it is intended that such matter be interpreted as illustrative and not in a limiting sense.

I claim:

1. A novel composition for applying a substantially water-insoluble bioactive reagent to the skins of animals, comprising an emulsion having a polymer containing said bioactive reagent, said polymer comprising particles which can agglomerate or coalesce upon evaporation of solvent for said emulsion, said polymeric particles being swellable upon contact with the skin oils of said animal, whereby said composition is adaptable for the controlled release of effective amounts of said bioactive reagent over an extended period of time.

2. A composition as defined in claim 1 wherein said bioactive reagent is selected from the group consisting of pesticides, bactericides and fungicides.

3. A composition as defined in claim 1 wherein said polymeric particles have a diameter no greater than about 50 microns prior to application.

4. A composition as defined in claim 1 wherein said polymeric particles are adaptable for agglomeration, upon solvent evaporation, to form particles which will retard rapid release of said contained bioactive reagent.

5. A composition as defined in claim 1 wherein said polymer is cross-linked.

6. A composition as defined in claim 5 wherein the cross-link density of said cross-linked polymer is sufficient to provide a predetermined desired release rate for said contained bioactive reagent, whereby to obtain application of an effective amount of said reagent for said extended period of time.

7. A composition as defined in claim 6 wherein said cross-linked polymer comprises a mixture of said polymer particles having varying cross-link densities.

8. A composition as defined in claim 1 further including an agent for facilitating rapid transport of said bioactive reagent, by capillary action, through the hairs of said animal towards the animal skin 9. A composition as defined in claim 8 wherein said agent for facilitating rapid transport comprises an anionic or non-ionic surfactant.

10. A composition as defined in cliam 9 wherein said bioactive reagent is a pesticide.

11. A compositon as defined in claim 10 wherein said pesticide is an ectoparasiticide.

12. A compositon as defined in claim 1 wherein said polymer, upon application, forms a film or agglomerate on said animal skin 13. A composition as defined in claim 1 wherein said bioactive reagent is dispersed or encapsulated in said polymer.

14. A novel composition for the topical application of a substantially water-insoluble bioactive reagent to the skin of an animal to provide a controlled release of effective amounts of said reagent over a period of time, said composition comprising an aqueous emulsion of a polymer retaining said reagent, said polymer comprising particles sufficiently small in diameter for penetration through the animal hair towards the skin, said polymer particles being characterized as being agglomeratable or coalescable upon evaporation of the aqueous solvent for said emulsion and by being swellable upon contact with skin oils of said animal.

15. A composition as defined in claim 14 wherein said polymer is cross-linked, the cross-link density being sufficient to lower the release rate for said bioactive reagent but insufficient to preclude effective release and subsequent diffusion of said effective amounts of reagent.

16. A composition as defined in claim 15 further including an agent for facilitating rapid transport of said bioactive reagent through the hairs of said animal toward the skin.

17. A composition as defined in claim 16 wherein said agent for facilitating rapid transport comprises a non-ionic surfactant.

18. A composition as defined in claim 17 wherein said bioactive reagent is a pesticide.

19. A composition as defined in claim 18 wherein said polymer comprises a terpolymer of 2-ethyl hexyl acrylate, ethyl acrylate and acrylic acid.

20. A composition as defined in claim 19 wherein said terpolymer is cross-linked with a difunctional monomeric cross-linking agent.

21. A composition as defined in claim 20 wherein said cross-linking agent comprises ethylene glycol dimethacrylate.

22. A process for providing an effective amount of a substantially water-insoluble bioactive reagent on or near the skin of a hairy animal for an extended time interval from a single application of said reagent, said process comprising the steps of:
  (1) applying on the surface of the body of said animal a quantity of said reagent greater than that needed to provide said effective amount at any given time within said time interval;
  (2) transporting at least a substantial portion of said applied reagent through said animal hairs toward said animal's skin;
  (3) diffusing a first portion of said quantity of reagent through skin oils produced by said animal, thereby providing an effective amount of said reagent at the beginning said time interval, while providing a barrier against diffusion of a second portion of said quantity of reagent in said skin oil; and (4) thereafter, slowly transporting said second portion through said barrier and into contact with said skin oils, thereby causing diffusion of effective amounts of said second portion throughout the remainder of said time interval.

23. A process as defined in claim 22 wherein said bioactive reagent is selected from the group consisting of pesticides, bactericides and fungicides.

24. A process as defined in claim 22 wherein said reagent is a ectoparasiticide.

25. A process as defined in claim 22 wherein said barrier compries agglomerated polymeric particles applied concurrently with said reagent at or near the skin or said animal, said polymeric particles being swellable by said skin oil whereby to permit said slow transporting of said second portion therethrough and into contact with said skin oils.

26. A process as defined in claim 24 wherein said reagent is initially contained in said polymer.

27. A method for treating an animal with an effective amount of a substantially water-insoluble bioactive reagent for an extended time interval from a single topical application containing said reagent, comprising the step of topically applying a composition as defined in claim 1.

* * * * *